US00PP19095P2

(12) United States Plant Patent
Heinrich

(10) Patent No.: US PP19,095 P2
(45) Date of Patent: Aug. 12, 2008

(54) ***LOBELIA* PLANT NAMED 'WESLOBLUE'**

(50) Latin Name: *Lobelia erinus*
Varietal Denomination: Wesloblue

(75) Inventor: Westhoff Heinrich, Südlohn (DE)

(73) Assignee: J. + H. Westhoff Interpel, Sdlohn (DE)

( * ) Notice: Subject to any disclaimer, the term of this patent is extended or adjusted under 35 U.S.C. 154(b) by 0 days.

(21) Appl. No.: 11/705,873

(22) Filed: Feb. 14, 2007

(51) Int. Cl.
*A01H 5/00* (2006.01)

(52) U.S. Cl. ..... Plt./451

(58) Field of Classification Search ..... Plt./451
See application file for complete search history.

*Primary Examiner*—Kent L Bell
*Assistant Examiner*—June Hwu
(74) *Attorney, Agent, or Firm*—C. A. Whealy

(57) ABSTRACT

A new and distinct cultivar of *Lobelia* plant named 'Wesloblue', characterized by its semi-upright and mounding plant habit; vigorous growth habit; freely branching habit and short internodes; dense and bushy plant form; continuously and freely flowering habit; and dark blue-colored flowers with small white-colored eyes.

1 Drawing Sheet

Botanical designation: *Lobelia erinus.*
Cultivar denomination: 'WESLOBLUE'.

BACKGROUND OF THE INVENTION

The present invention relates to a new and distinct cultivar of *Lobelia,* botanically known as *Lobelia erinus* and hereinafter referred to by the name 'Wesloblue'.

The new *Lobelia* is a product of a planned breeding program conducted by the Inventor in Südlohn, Germany. The objective of the breeding program is to create new *Lobelia* cultivars with good vigor and attractive flower coloration.

The new *Lobelia* originated from a cross-pollination made by the Inventor in 2003 of a proprietary seedling selection of *Lobelia erinus* identified as code number 03P746, not patented, as the female, or seed, parent with a proprietary seedling selection of *Lobelia erinus* identified as code number 03P509, not patented, as the male, or pollen, parent. The new *Lobelia* was discovered and selected by the Inventor as a single flowering plant with the progeny of the stated cross-pollination grown in a controlled environment in Südlohn, Germany.

Asexual reproduction of the new cultivar by terminal cuttings in Südlohn, Germany since 2004, has shown that the unique features of this new *Lobelia* are stable and reproduced true to type in successive generations.

SUMMARY OF THE INVENTION

Plants of the cultivar Wesloblue have not been observed under all possible environmental conditions. The phenotype may vary somewhat with variations in environment such as temperature and light intensity without, however, any variance in genotype.

The following traits have been repeatedly observed and are determined to be the unique characteristics of 'Wesloblue'. These characteristics in combination distinguish 'Wesloblue' as a new and distinct cultivar of Lobelia:

1. Semi-upright and mounding plant habit.
2. Vigorous growth habit.

3. Freely branching habit and short internodes; dense and bushy plant form.
4. Continuously and freely flowering habit.
5. Dark blue-colored flowers with small white-colored eyes.

Plants of the new *Lobelia* differ from plants of the female parent selection in the following characteristics:

1. Plants of the new *Lobelia* are more vigorous than plants of the female parent selection.
2. Leaves of plants of the new *Lobelia* are pubescent whereas leaves of plants of the female parent selection are glabrous.
3. Plants of the new *Lobelia* and the female parent selection differ in flower color as plants of the female parent selection have pink-colored flowers.

Plants of the new *Lobelia* differ from plants of the male parent selection in the following characteristics:

1. Plants of the new *Lobelia* have smaller flowers than plants of the male parent selection.
2. Plants of the new *Lobelia* have smaller sepals than plants of the male parent selection.
3. Plants of the new *Lobelia* and the male parent selection differ in flower color as plants of the male parent selection have light violet-colored flowers.

Plants of the new *Lobelia* can be compared to plants of the cultivar Wesloarc, disclosed in U.S. Plant Pat. No. 15,871. In side-by-side comparisons conducted in Südlohn, Germany, plants of the new *Lobelia* differed from plants of the cultivar Wesloarc in the following characteristics:

1. Plants of the new *Lobelia* had finer lateral branches than plants of the cultivar Wesloarc.
2. Plants of the new *Lobelia* had smaller leaves than plants of the cultivar Wesloarc.
3. Plants of the new *Lobelia* had smaller flowers than plants of the cultivar Wesloarc.
4. Flowers of plants of the new *Lobelia* were darker blue in color than flowers of plants of the cultivar Wesloarc.
5. Flowers of plants of the new *Lobelia* had smaller white eyes than flowers of plants of the cultivar Wesloarc.

Plants of the new *Lobelia* can be compared to plants of the cultivar Weslobigblue, disclosed in U.S. Plant Pat. No. 12,634. In side-by-side comparisons conducted in Südlohn, Germany, plants of the new *Lobelia* differed from plants of the cultivar Weslobigblue in the following characteristics:

1. Plants of the new *Lobelia* were more upright and shorter than plants of the cultivar Weslobigblue.
2. Plants of the new *Lobelia* had shorter internodes than plants of the cultivar Weslobigblue.
3. Plants of the new *Lobelia* had smaller flowers than plants of the cultivar Weslobigblue.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Lobelia*.

The photograph at the top of the sheet comprises a side perspective view of a typical flowering plant of 'Wesloblue' grown in a container.

The photograph at the bottom of the sheet is a close-up view of a typical flower of 'Wesloblue'.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photographs and following description were grown under conditions which closely approximate commercial production conditions during the spring and summer in a glass-covered greenhouse in Südlohn, Germany for about 20 weeks in containers. During the production of the plants, day temperatures ranged from 20° C. to 25° C., night temperatures ranged from 16° C. to 18° C. and light levels ranged from 3,000 lux to 50,000 lux. Plants were pinched one time about two weeks after planting.

Botanical classification: *Lobelia erinus* cultivar Wesloblue.

Parentage:

*Female parent.*—Proprietary seedling selection of *Lobelia erinus* identified as code number 03P746, not patented.

*Male parent.*—Proprietary seedling selection of *Lobelia erinus* identified as code number 03P509, not patented.

Propagation:

*Type cutting.*—Terminal vegetative cuttings.

*Time to initiate roots.*—About 14 to 18 days at 18° C. to 20° C.

*Time to produce a rooted young plant.*—About 21 to 24 days at 18° C. to 20° C.

*Root description.*—Fine, fibrous.

*Rooting habit.*—Freely branching.

Plant description:

*Form.*—Semi-upright and mounding plant habit. Freely branching habit with lateral branches developing at potentially ever node; short internodes; dense and bushy plant habit. Vigorous growth habit.

*Plant height.*—About 18 cm to 22 cm.

*Plant width.*—About 35 cm to 45 cm.

*Lateral branch description.*—Length: About 13 cm to 21 cm. Diameter: About 1.1 mm. Internode length: About 1 cm. Strength: Strong. Texture: Pubescent. Color: 146A.

Foliage description:

*Arrangement.*—Alternate, simple; sessile.

*Length, basal leaves.*—About 3.7 cm.

*Width, basal leaves.*—About 1.7 cm.

*Shape.*—Oblong to oblanceolate.

*Apex.*—Emarginate to acute.

*Base.*—Attenuate.

*Margin.*—Crenate.

*Texture, upper and lower surfaces.*—Pubescent; leathery.

*Venation pattern.*—Pinnate; arcuate.

*Color.*—Developing foliage, upper surface: 137A. Developing foliage, lower surface: 137C. Fully expanded foliage, upper surface: 137A; venation, 137A. Fully expanded foliage, lower surface: 138A; venation, 138A.

Flower description:

*Flower arrangement/shape.*—Flowers arranged singly at lateral apices. Flowers held mostly outwardly. Flowers persistent. Flowering freely and continuously; older flowers are overgrown by new flowers and foliage. Flowers not fragrant. Flowers tubular with three larger lower petals and two upright petals.

*Natural flowering season.*—Spring until frost in the Germany.

*Flower longevity on the plant.*—Longevity of individual flowers is highly dependent on weather conditions; typically about one week.

*Flower size.*—Diameter: About 1.8 cm. Depth (height): About 2 cm. Flower throat diameter: About 3.9 mm. Flower tube length: About 7 mm. Flower tube diameter, at the base: About 2 mm.

*Flower buds.*—Length: About 9 mm. Diameter: About 3 mm. Shape: Oblong. Color: 194B to 194C.

*Petals.*—Arrangement: Single whorl of five petals, fused; three larger lower petals and two smaller upper petals. Three lower petals: Shape: Oblong. Length, above throat: About 1 cm. Width: About 6 mm. Two upper petals: Shape: Spatulate. Length, above throat: About 6 mm. Width: About 2 mm. Upper and lower petals: Apex: Obtuse to cuspidate. Margin: Entire. Texture, upper and lower surfaces: Smooth, glabrous. Color, upper and lower petals: When opening, upper surface: 95A to 96A; eye, 155A. When opening, lower surface: 94D. Fully opened, upper surface: 96A; towards base of lower petals, small white eye, 155A, with small spots, 93A; color becoming closer to 95A with development. Fully opened, lower surface: 97B. Throat: 155A; small spots, 93A. Tube: 94B becoming closer to 97D.

*Sepals.*—Arrangement: Single whorl of five sepals, fused at the base: star-shaped calyx. Length: About 4 mm. Width: About 1 mm. Shape: Acicular. Apex: Acute. Margin: Entire. Texture, upper and lower surfaces: Pubescent. Color, upper and lower surfaces: 137A.

*Peduncles.*—Length: About 2.2 cm. Diameter: About 0.8 mm. Texture: Pubescent. Color: 137A.

*Reproductive organs.*—Stamens: Quantity per flower: About five. Anther length: About 2 mm. Anther color: 187A. Pollen amount: Moderate. Pollen color:

5A. Pistils: Quantity per flower: One. Pistil length: About 1 cm. Stigma shape: Two-parted, ovate. Stigma color: N187A to N187B. Style length: About 5 mm. Style color: 144B. Ovary color: 138A to 138B.

*Seed/fruit.*—Seed and fruit production has not been observed.

Disease/pest resistance: Plants of the new *Lobelia* have not been noted to be resistant to pathogens and pests common to *Lobelia.*

Temperature tolerance: Plants of the new *Lobelia* have been observed to tolerate temperatures from about 4° C. to about 30° C.

It is claimed:

1. A new and distinct *Lobelia* plant named 'Wesloblue' as illustrated and described.

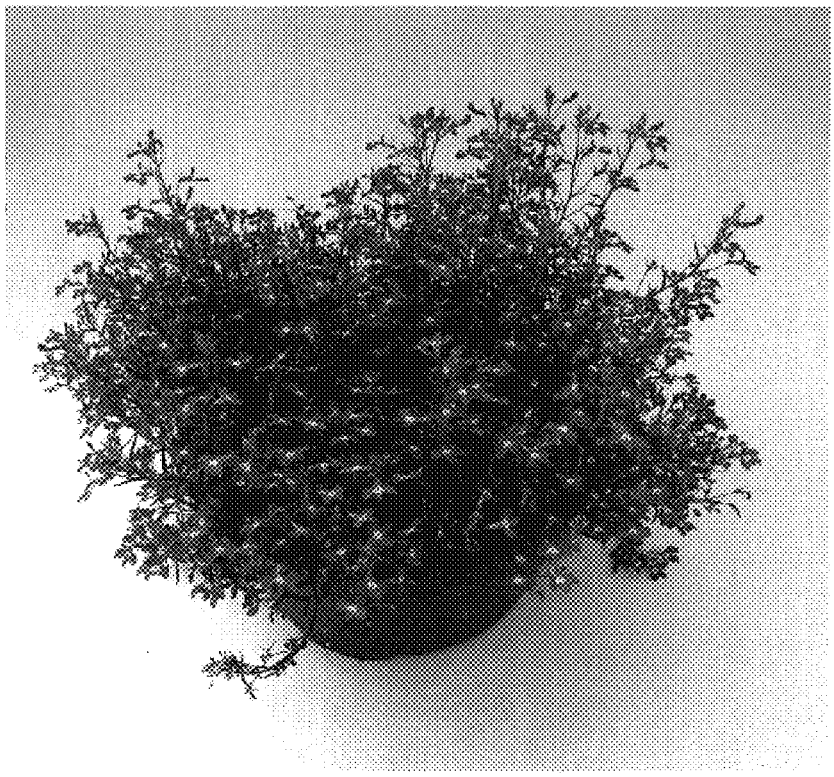
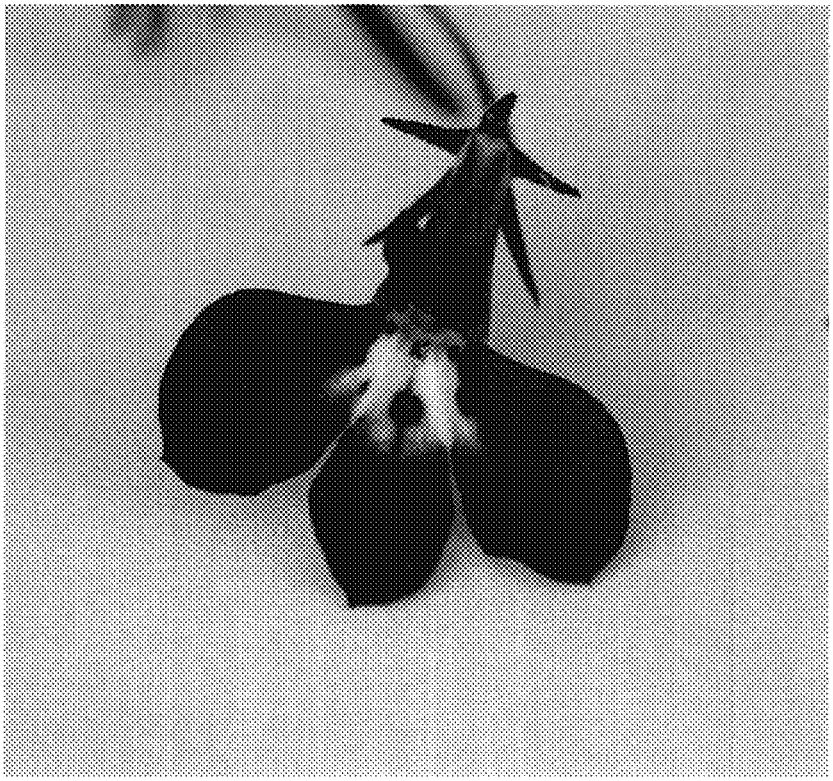

* * * * *